United States Patent [19]

Stonestrom

[11] 4,284,896
[45] Aug. 18, 1981

[54] COMPUTERIZED TOMOGRAPHIC RECONSTRUCTION METHOD AND SYSTEM UTILIZING REFLECTION

[75] Inventor: James P. Stonestrom, Palo Alto, Calif.

[73] Assignee: General Electric Company, Milwaukee, Wis.

[21] Appl. No.: 69,658

[22] Filed: Aug. 24, 1979

[51] Int. Cl.$^3$ .................................................. A61B 6/00
[52] U.S. Cl. .................................. 250/445 T; 364/414
[58] Field of Search ..................... 250/445 T; 364/414

[56] References Cited

U.S. PATENT DOCUMENTS

| | | | |
|---|---|---|---|
| 4,126,787 | 11/1978 | Hounsfield | 250/445 T |
| 4,149,249 | 4/1979 | Pavkovich | 364/414 |
| 4,176,279 | 11/1979 | Schwiecz et al. | 250/445 T |

*Primary Examiner*—Alfred E. Smith
*Assistant Examiner*—T. N. Grigsby
*Attorney, Agent, or Firm*—Douglas E. Stoner; Dana F. Bigelow

[57] ABSTRACT

An improvement is disclosed which is applicable to the method for constructing a two-dimensional representation of an object slice lying in a quasi-plane by positioning a radiation source providing a fan beam incident on the object, positioning detector means opposite the source and aligned therewith and lying in said quasi-plane for detecting radiation in said quasi-plane not absorbed or scattered by the object; effecting relative rotation between the object and the source-detector combination about an axis of rotation such that the source and detector means remain in the quasi-plane; effecting measuring projections from the source at a plurality of angular positions during the rotation to obtain a multiplicity of measured data readings from the detectors at each said projection; and reconstructing a two-dimensional representation of the object slice by convolving the data without reordering same, and scaling and back projecting same. Pursuant to the improvement, estimated detector data is generated at desired projection angles, by reflecting the measured detector data obtained during the said measuring projections, and the reconstruction step is performed utilizing both the measured and the estimated detector data. A system embodiment of the invention is also disclosed and claimed.

9 Claims, 7 Drawing Figures

COMPUTERIZED TOMOGRAPHIC RECONSTRUCTION METHOD AND SYSTEM UTILIZING REFLECTION

BACKGROUND OF INVENTION

This invention relates generally to non-desctructive testing, relates more specifically to medical diagnostic apparatus and methodology; and yet more specifically, relates to X-ray scanning apparatus and methodology of the type associated with computed tomography.

Within recent years much interest has been evidenced on the part of medical diagnosticians in the field now widely known as "computed tomography" sometimes referred to hereinafter as "CT". In a typical procedure an X-ray source and detector apparatus are positioned on opposite sides of the portion of the patient which is intended for examination. In early prior art these paired elements are made to transit across the body portion to be examined while the detectors measure the X-ray absorption at the plurality of transmission paths defined during the transit process. Periodically as well, the paired source and detector means are rotated to a different angular orientation about the body and the transit process repeated. A very high number of absorption values may be yielded by procedures of this type and the relatively massive amounts of data thus accumulated are processed by a digital computer which correlates the absorption values, to thereby derive absorption values for a very high number of points (typically in the thousands) within the section of the body being scanned.

This point-by-point data can then be combined to enable reconstruction of a matrix (visual or otherwise), which constitutes an accurate depiction of the density function of the bodily section examined. The skilled diagnostician by considering one or more of such sections can often diagnose various bodily ailments such as tumors, blood clots, etc., which features would be difficult if not impossible to effectively locate by prior art methodology.

Later developments in the computer tomography field are demonstrated in the co-pending application of John M. Pavkovich and Craig S. Nunan, Ser. No. 643,894, filed Dec. 23, 1975, and entitled "Tomographic Apparatus and Method for Reconstructing Planar Slices from Non-Absorbed Radiation" and in the co-pending application of John M. Pavkovich entitled "Apparatus and Method for Reconstructing Data", filed Dec. 23, 1975 under Ser. No. 643,896. Both of these applications are assigned to the same assignee as is the present application.

The apparatus disclosed in the above-cited applications utilizes a fan beam source of radiation coupled with application of a convolution method of image reconstruction with no intervening reordering of fan rays, to thereby eliminate the errors and delay in computation time which would otherwise be involved in such reordering. The radiation source and detector means are positioned on opposed sides of the portion of the patient being examined and these elements are made to rotate through a revolution or portion thereof while the detectors measure the radiation absorption at the plurality of transmission paths defined during the rotational process.

In a typical apparatus embodiment of the Pavkovich and Pavkovich et al type of apparatus, an assembly is provided, which is rotatable about an axis extending along a central opening defined therein, together with means for positioning the bodily portion to be examined within the central opening so that the axis of assembly rotation is perpendicular to a thin generally planar section of the body portion being scanned. A source of penetrating radiation, i.e., of X-rays or gamma rays is mounted on the assembly toward one side thereof, and provides radiation in the form of a fan beam. Means are provided for rotating the assembly so that the fan beam impinges upon the bodily portion at a plurality of incident directions. Detection is enabled by means positioned on the assembly opposite the source, which thus detects non-absorbed radiation proceeding laterally along the section.

Reference may further be usefully had to U.S. Pat. No. 4,149,249 which issued on Apr. 10, 1979 to the aforementioned John M. Pavkovich, which patent is assigned to the assignee of the present application. The said patent entitled "Apparatus and Method for Reconstructing Data" further illustrates the apparatus and methodology to which the present invention is directly applicable, and the disclosure of said patent is incorporated herein by reference.

In the U.S. Pat. No. 4,149,249, apparatus of the general type previously described is set forth, together with reconstruction means which are coupled to the detector means, and which may comprise a general purpose computer, a special purpose computer, and control logic for interfacing between these computers and controlling the respective functions thereof for permitting a convolution and back projection based upon non-absorbed and non-scattered radiation detected by the detector means. Display means are coupled to the reconstruction means for providing a visual or other display or representation of the quantities of radiation absorbed at the points considered in the object.

If the course of obtaining the detector data from which the image reconstruction is effected, it has been usual practice to effect the aforementioned relative rotation of the source detector array with respect to the patient over a time period of approximately 1 to 15 seconds (with 3 seconds being typical) while taking readings of absorbed radiation received by the detector means. The latter may be of the types disclosed in the above references. The detector means thus typically comprises of the order of 301 individual detector cells or elements which are effectively in side-by-side relationship. The source may be operated continuously, but is more often operated in pulsed fashion, and typically a set of measurements is taken at each successive 1° increment of rotation (preferably by pulsing the source on at each said 1° position), so that 360×301 values of measured (transmitted) radiation are obtained during each 360° cycle of rotation.

In order to increase the available resolution possible from processing of the collected detector data, it would in principle be highly desirable to increase the number of detector elements positioned to detect the fan beam. In practice, however, both size and cost limitations have rendered this relatively impractical.

For various reasons it would further be desirable in operation of a computerized tomography system to be able to effect data collection during less than a full revolution of the gantry or platform carrying the source and detector elements undergoing planetary motion about the scanned object. Such a procedure would be desirable, partially in order to shorten the period during which the patient is required to remain motionless; and additionally, to reduce the total incident radiation to which the patient is exposed. In the past, however, efforts to operate in the aforementioned manner have not been successful since measuring projections are missing, which in the past have either been arbitrarily estimated or have been taken to be zero. These assumptions have lead to undesirable artifacts and loss of definition in the resultant reconstructed image.

It is in principle also of interest to the technician in the present field of application, to be able to study dynamic events as, for example, in performing cardiac studies, where one is often interested in examining a section through portions of the heart at selected phases of the cardiac cycle.

Similarly, it is of interest to study other medically significant dynamic events such as blood flow, which may have extreme value in diagnosing aortical aneurisms, infarctions, or the like. In the co-pending application of Edward J. Seppi et al., Ser. No. 789,910, filed Apr. 22, 1977 and entitled "Method and System for Cardiac Computed Tomography", which again is assigned to the assignee of the present invention, a method and system is disclosed which is applicable to the aforementioned type of studies. In this system data is acquired during one or more full rotational cycles and suitably stored. The data corresponding to various angular projections can then be correlated with the desired portions of the object's cyclical motion by means of a reference signal associated with the motion, such as that derived through an electrocardiagram where a heart is the object of interest. In systems and approaches of the types as mentioned, however, projections are invariably missing, i.e., a full 360° collection of projections are not usually present; and partially for this reason the image resolution and quality, again as aforementioned, can be quite unsatisfactory.

In accordance with the foregoing, it may be regarded as an object of the present invention to provide a method and system applicable to computerized tomography systems of the type heretofore discussed, which enables an increase in available resolution and image quality possible from processing of the collected detector data, by effectively increasing the number of detectors positioned to detect the fan beam.

SUMMARY OF INVENTION

Now in accordance with the present invention, an improvement is disclosed which is particularly applicable to the method wherein one constructs a two-dimensional representation of an object slice lying in a quasi-plane by the steps of positioning a radiation source for providing radiation in the form of a fan beam so that at least some of the radiation passes through the object; positioning detector means including an array of side-by-side detector elements opposite the source and aligned therewith and lying in the quasi-plane for detecting radiation in the quasi-plane not absorbed or scattered by the object; effecting relative rotation between the object and the source-detector combination about an axis of rotation such that the source and detector means remain in the quasi-plane; effecting measuring projections from the radiation source at a plurality of angular positions during the rotation to obtain a multiplicity of measured data readings from the detector array at each said projection; and reconstructing a two-dimensional representation of the object slice by convolving the data without reordering of same, and scaling and back projecting same.

According to the improvement of the invention, estimated detector data is generated at desired projection angles by reflecting the measured detector data, and the reconstruction step is performed utilizing both the said measured and said estimated detector data.

The aforementioned reflecting step includes adjusting the measured readings from each detector element by interpolating between adjacent (i.e., successive) readings from the specified detector element, to yield the reading appropriate for geometrical reflection to the said desired projection angle.

In one aspect of the invention the effective number of detector elements may be increased, for example, by a factor of two, to thereby considerably increase the resolution possible from a given detector array. In this application of the invention the reflected data corresponds to detector element positions laterally displaced with respect to the positions of such detector elements during the projections which yield the measured detector data.

In a further aspect of the invention the desired projection angles are additional to the projection angles at which the detector data is measured, thereby effectively providing additional projections, i.e., beyond those actually carried out.

In one aspect of the last approach the measuring projections are effected over less than a full of 360° rotation, e.g., over an angle of perhaps 215° (180°+fan angle). The measured readings from these projections are reflected to generate the said estimated detector data at projection angles required to complete a set of projections for the full 360° rotation.

The measuring projections may further be effected during one or more full rotations of the source-detector means; and projection sets corresponding to less than the full number of projection sets thus generated may be selected. Thereupon, one may utilize the selected sets by reflecting the data of same to create detector data at the said desired additional projection angles. The selected projection sets can, e.g., correspond to a selected time sub-interval of the total rotation period for effecting the measuring projections, thereby enabling reconstruction of an image corresponding to a foreshortened sub-interval in time of the total rotation period.

The selected projection sets can also coincide with a preselected event occurring during the total rotation period. By way of illustration, one may desire to study one particular phase of a dynamic event as, for example, a particular portion of the cardiac cycle. Accordingly, one may select sets of measuring projections corresponding to the occurrence of the said event, and utilizing said selected sets reflect the data of same to create detector data at additional projection angles, thereby enabling from the resultant augmented projection data, an image having much improved quality.

BRIEF DESCRIPTION OF DRAWINGS

The invention is diagrammatically illustrated, by way of example, in the drawings appended hereto, in which.

DESCRIPTION OF THE PREFERRED EMBODIMENTS

Figure 1:
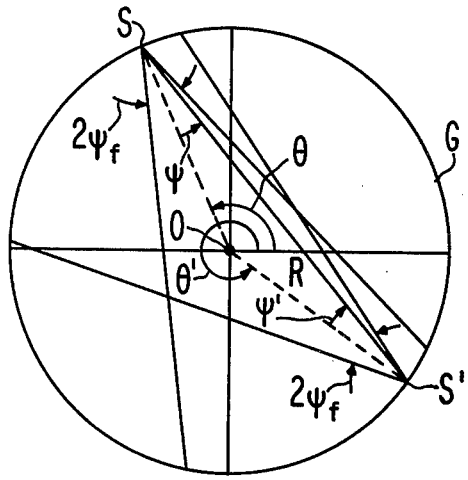
FIG. 1 is a schematic diagram illustrating the basic geometry of reflection.

In FIG. 1 a schematic geometrical figure is set forth which illustrates basic geometrical relationships deemed useful in consideration of the present invention. Initially, it may be noted that while the rotary fan beam scanning modality which is utilized in apparatus of the type to which this invention is addressed—i.e., as in the Pavkovich Ser. No. 760,492 application—does not have the trivial 180° angular symmetry obtained with parallel ray scanning (e.g., translate-rotate systems), the rotary fan geometry (despite a somewhat distorted symmetry) results in effective measurement of each ray twice over the 360° rotation.

As thus illustrated in FIG. 1, the same line integral measurements would occur with the source occupying each end S or S' of the same ray R. Thus, essentially there is a twofold redundancy in the fan-projection data that can be exploited by the reconstruction algorithm utilized in the systems of the present type, to improve either the spatial or temporal resolution of the reconstructed image.

Referring further to FIG. 1, it will be appreciated that G schematically represents the rotatable platform or so-called gantry, upon which the radiation source is mounted in opposition to a detector bank or array (which is not explicitly shown). Details of such construction again are set forth in the referenced disclosures, including those of Pavkovich.

The projection data measured by the rotary fan can be described by $L(\theta,\psi)$ where $\theta$ indicates the viewing angle, or the X-ray source position, and $\psi$ indicates the angle of a ray within the fan beam, with S and S' indicating positions of the X-ray source. The total fan angle is therefore $2\psi_f$. Also to be noted is that the same ray R has coordinates $(\theta,\psi)$ and $(\theta', \psi')$. The first coordinate set corresponds to a measurement with the radiation source positioned at S. In the second identification, the source is regarded as positioned at S'. It is noted that in the foregoing:

$$\theta' = \theta + \pi + 2\psi \quad (1a)$$

and $$\psi' = -\psi \quad (1b)$$

The above geometric relationships specify that $L(\theta,\psi)$ and $L(\theta',\psi')$ are two equivalent measurements of the ray considered, or $$L(\theta',\psi') = L(\theta + \pi + 2\psi, -\psi) \quad (2)$$

Defining $L_M(\theta,\psi)$ as the measured data (line integral), and $L_R(\theta',\psi')$ as the reflected data, it follows from (1) and (2) that $$L_R(\theta',\psi') = L_M(\theta,\psi) \quad (3)$$

and $$L_R(\theta',\psi') = L_M(\theta' - \pi + 2\psi', -\psi')$$

Equation (3) indicates that by the process of reflection, the missing line integrals, $L_R(\theta',\psi')$, at a particular viewing angle, $\theta'$, can be estimated from the measurements, $L_M(\theta' - \pi + 2\psi', -\psi')$, for all possible ray angles, $\psi'$ ($-\psi_f \leq \psi' \leq \psi_f$, where $2\psi_f$ indicates the fan angle.)

It can further be seen by reviewing the above equations, and by examination of FIG. 1, that each reflected view extends across $4\psi_f$, which means that its computation requires measured data from within twice the fan angle worth of gantry rotation.

The measurements generated by the scanning process consist of a set of uniformly spaced samples in both the viewing angle $\theta$ and the ray angle $\psi$. This discretization takes place in a system of the type considered in the present application, at intervals of $\Delta\theta = 1°$, and $\Delta\psi = 0.11°$. Thus, the detector angular spacing is approximately 10 times finer than the source position angular spacing. To compute the ray $L_R(\theta',\psi')$, it is desired to use $L_M(\theta' - \pi + 2\psi',\psi')$. However, for $\psi' \neq 0$, a measurement will not necessarily exist at the desired angle $\theta' - \pi + 2\psi'$. Thus, to compute $L_R$, in accordance with the invention it has been found appropriate to interpolate the $L_M(\theta,\psi)$ to the desired angle $\theta' - \pi + 2\psi'$. An interpolation, which can be cubic or of other form, between successive source positions has been found appropriate for this purpose. This aspect of the present invention will be further discussed hereinbelow.

Figure 2:
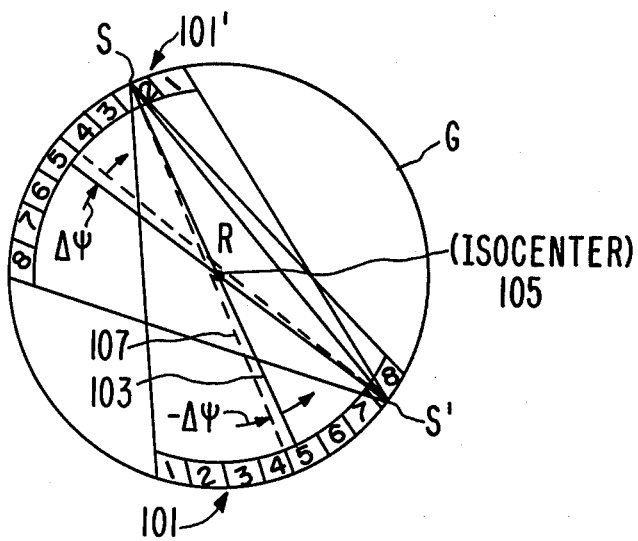
FIG. 2 is a geometrical diagram similar to FIG. 1 and illustrating further considerations arising from possible detector offset.

A further factor for consideration in practice of the invention, is illustrated in the geometrical representation of FIG. 2. This involves use of the proper angular offset of the detector array.

In FIG. 2 the detector array is schematically depicted at 101 and 101'. The position 101 corresponds to that wherein measurement data is taken during a measurement projection from a source at S. The position 101' is where reflected data is to be estimated, i.e., the detector array may not actually make a set of measurements at this zone—or at least may not be positioned precisely as shown.

In each instance the detector array has been exaggerated in dimensions and purposes of clarity. Only eight individual detector elements are depicted—these being schematically shown. In practice 301 detectors are commonly utilized in the array of the type employed in the apparatus to which the invention is especially applicable, although differing numbers of cells can be used. Also, the array is not necessarily curve-linear in form, although such arrangement can be utilized.

The line 103 passes from the source S through the so-called isocenter 105, which is the center of rotation of the source-detector combination. The line 107 represents the path between the source S and the geometrical center of array 101. Thus, in the present instance line 107 passes directly between elements 4 and 5 of array 101. To be noted, however, is that this center of the array is displaced from line 103, i.e., line 107 is displaced from line 103 by an angle $\Delta\psi$. This represents an angular offset of the detector array which is a design feature that is sometimes utilized in apparatus of the type to which the present invention is applicable in order to improve the system's spatial resolution.

It has thus been shown, and is therefore known, that the spatial resolution yieldable in a tomographic scanning apparatus wherein the angle of rotation of the radiation source about the patient is greater than 180°, is improved by offsetting the alignment of the detector array elements relative to a line passing from the source through the center of rotation. In consequence of such arrangement the source-detector element path defined at each projection angle through the bodily portion being examined by the apparatus, differs for all said paths at each of the projection angles. The consequential increase in implied information for the data generated during a 360° rotation, enables increased image resolution upon processing of the said data.

By virtue of the said offset $\Delta\psi$, it will be clear that a corresponding opposite offset-$\Delta\psi$ exists in the reflected projection data, as shown in the Figure. This effectively introduces a lateral displacement of the detector array. The significance of this will be further discussed hereinbelow.

Figure 3A:
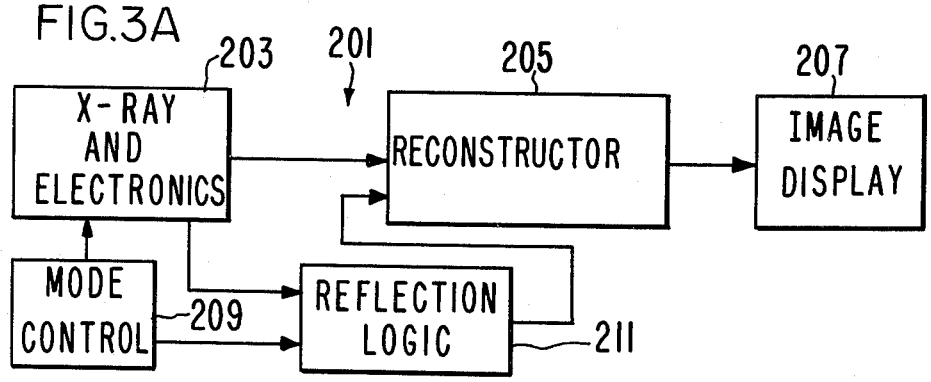
FIGS. 3A and 3B are simplified electronic block diagrams illustrating the manner in which the method of the invention may be implemented in a conventional computerized tomography apparatus.
Figure 3B:
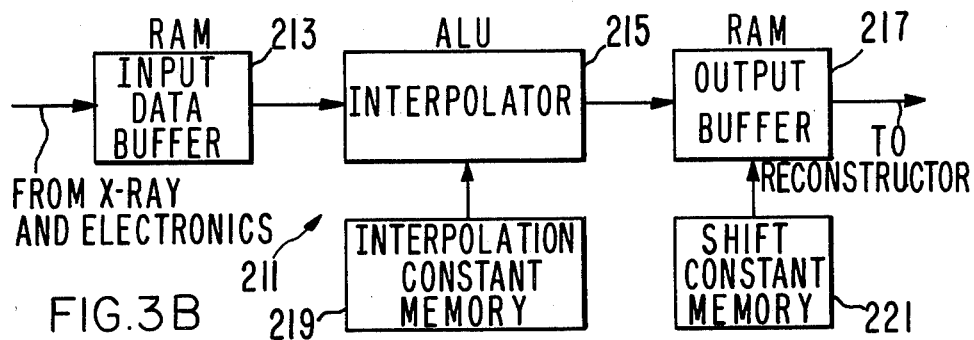
Figure 4:
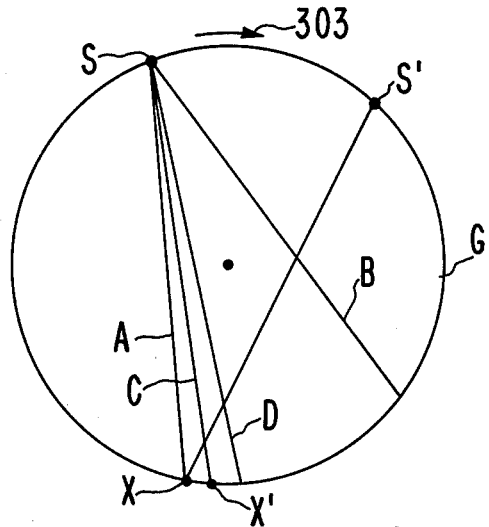
FIG. 4 is a further geometrical diagram illustrating additional parameters useful in consideration of reflection.

The manner in which the method of the present invention is applied to a number of highly significant and useful purposes may be further appreciated by reference to FIGS. 3 through 5 herein.

In FIG. 3A a simplified electronic block diagram appears, illustrating on a much simplified scale, a computerized tomography system 201 incorporating means to implement the method of the invention. The X-ray and electronics means 203, reconstructor 205, and image display means 207, can in total be regarded as representing a prior art CT system, corresponding, for example, to the system of this type disclosed in the aforementioned Pavkovich application Ser. No. 760,492.

In the present instance the data proceeding from X-ray and electronics means 203 basically can be considered as representing the raw data output from the detectors. A set of 301 pieces of such raw detector data is typically generated at each discrete projection angle at which such a measurement is made. In some instances there will representatively be 360 such sets of data, i.e., a measuring projection being effected at each 1° angle during a full single rotation of the apparatus gantry. However, application of the present invention can in many instances of importance and interest enable data to be taken at much less than during the total rotation of the said gantry. For example, it is practical by application of the invention, to only take such data over a 215° span of rotation, so that but 215 sets of 301 pieces of data need be generated. Other arrangements are also possible, as will be further discussed.

In any and all of these events under actuation from mode control means 209, the data proceeding from X-ray and electronics means 203 is diverted through reflection logic 211 where such data is reflected and then provided to reconstructor 205. Reflection logic 211 operates on the raw detector data provided thereto to provide the desired reflected data. Reflector logic 211 can include a memory means (such as a RAM), a multiplier means, an adding means, and control circuitry for these elements; the rate of processing can be increased by including in logic 211 one set of the foregoing elements for each processing channel associated with a detector element.

Further details of reflection logic 211 appear in FIG. 3B. Raw detector data from X-ray and electronics means 203 is provided to input data buffer 213 (a RAM) via mode control 209 (FIG. 3A). The data is then interpolated at an arithmetic logic unit (ALU) 215 using interpolation constants from a memory 219 (a RAM or ROM). The interpolation constants utilized depend upon the interpolation scheme chosen.

The interpolated data is transferred to an output buffer 217, to specific locations in the buffer in accordance with shift constants furnished from a memory 221. These shift constants are determined by application of Equations 1a and 1b. Flow of the data into, out of, and through the elements of FIG. 3B is effected under control of logic at mode control 209 (for the sake of clarity the control lines from same are not shown).

The memory means of logic 211 can serve so that in a given instance data, for example acquired during a full rotation, is collected and held in such memory, where it can be further processed in selective fashion and then furnished to reconstructor 205.

For example, where it is desired to study a phase of a cardiac cycle in a patient being examined, the heart of the patient can be scanned for at least one full 360° rotation (preferably four full rotations) of the apparatus gantry, and the selected set of projections provided to the memory at logic 211. As is taught in the co-pending application of Edward J. Seppi et al., Ser. No. 789,910, filed May 31, 1977 and assigned to the assignee of the present application, projections of interest to a particular phase of a cardiac cycle can be readily identified by occurrence of characteristic pulses in the electrocardiogram. Thus, by application of the techniques in the aforementioned application, the projection sets of interest may be withdrawn from the said memory. The withdrawn sets will be such that numerous projection angles will be absent. By means of the present invention, however, the sets may be processed by reflection to provide some or all of the missing projections, and then furnished to reconstructor 205 to enable the image reconstruction.

The raw data from X-ray and electronics means 203 need not necessarily be provided to a memory. It can alternatively be processed "on the fly". For example, in the cardiac application just cited, the projection sets can be directly collected as they are generated, with other projection sets being generated but ignored, or with the X-ray tube not being activated or pulsed during the projections which are not of interest.

As has been previously stated, the method of the invention is also applicable to that situation wherein one desires to increase the image resolution obtainable from use of a given number of detector elements. For example, in the representative type of apparatus heretofore discussed, the number of such detector elements is 301 but one would desire in many instances to increase the resolution to a level which would be obtainable were twice the number of detectors actually present in the detector array.

Pursuant to the method of the present invention, one effects just such a result by reflecting data obtained during a measuring projection to a plurality of reflected points on the opposed side of the gantry. The points to which such measured data is reflected correspond to detector element positions laterally displaced with respect to the positions of such elements during the projections yielding the measured detector data. This is accomplished by interpolating between successive data readings of a given detector to yield the reading appropriate for geometrical reflection to the desired projection angle in accordance with Equation 3.

The foregoing technique is implemented in the system 201 in the manner heretofore discussed typically, e.g., under control of mode control means 209, the raw detector data generated during a full rotation can be provided from X-ray and electronics means 203 to reflection logic 211, where among other possibilities it can be stored in a memory for processing to reflect such collected data as above described; or again, as previously described, the data need not necessarily be stored in memory, but can be processed as it is collected. In all events, it is then provided to the reconstructor 205, from which the final image display is enabled at means 207.

In one approach directed toward increasing image resolution, the reflected data correspond to detector element positions laterally displaced with respect to the positions of the actual detector elements of the measuring apparatus. In one implementation of the foregoing, measured detector data from each measuring projection angle is stored in a memory (which can form part of electronics block 203) and interleaved with the estimated detector data obtained by reflection and corresponding to the same projection angle. The resulting interleaved data is furnished to the reconstructor as if it had come from a detector array with a higher density of elements.

In another implementation of the foregoing, measured projection data from each measuring projection angle is interleaved with zeros and provided to the reconstructor as if it had come from a detector array with a higher density of elements. Similarly, the reflected data corresponding to each measuring projection angle is interleaved with zeros and also furnished to the reconstructor. Since reconstructor 205 operates in a linear fashion upon the data presented thereto (as taught in the referenced Pavkovich Ser. No. 760,492 application), the resultant treatment of the totality of data provided to the reconstructor is fully equivalent to that which occurs in the implementation described in the preceding paragraph. Furthermore, the interleaving of zeros in the several instances above described can if desired be carried out by a simple modification of the reconstructor 205.

In FIGS. 4 and 5 herein further schematic diagrams appear, useful in understanding the manner in which the present invention operates and serves to achieve the results aforementioned.

FIG. 4 is generally similar to FIG. 1, and illustrates a gantry G of typical CT apparatus of the type heretofore discussed. The gantry can be assumed for purposes of the present discussion to rotate in the direction of arrow 303 during a scanning operation. If the gantry G is assumed to undergo a full 360° rotation and if it is further assumed in accordance with a typical practice that a set of measuring projections are produced at each discrete 1° angle, then with the detector array consisting of 301 detectors, it will be evident that 360 measuring projections are obtained, each consisting of 301 measured values.

Figures 5A, 5B:
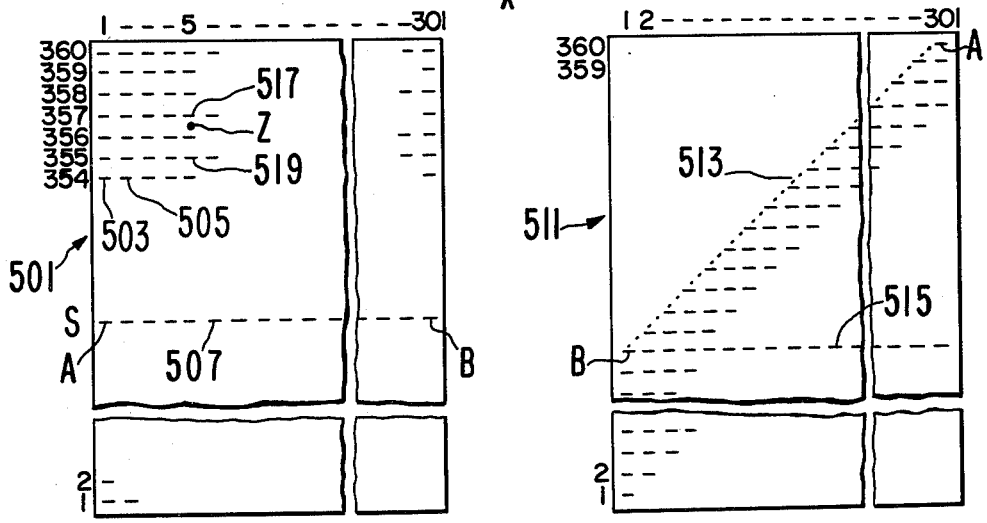
FIGS. 5A and 5B are schematic diagrams useful in understanding the transformation of data which is effected pursuant to the reflection process of the invention.

The resultant collected data is schematically depicted at FIG. 5A, which illustrates a data set 501 for the acquired raw measuring data. The detector element numbers, running from 1 to 301 appear at the top edge of data set 501; the numbers at the left margin running from 1 to 360 correspond to the plurality of angles of the measuring projections. The data of each measuring projection is therefore represented on data set 501 as a line consisting of the readings, e.g., 503, 505, etc. of the successive detector elements. It is also seen that under a given detector element, such as element #5, the measured data values are arrayed in a column.

At a given measuring projection such as with the source at S, a fan beam bounded by rays A and B generates 301 data measurement values. These are seen to appear in data set 501 at line 507. The measured values corresponding to rays A and B are seen to be at the end points of line 507.

It may now be assumed that the entirety of data points appearing on data set 501 are reflected in accordance with the method of the invention, to produce what could be regarded as a derived reflected data set 511, which appears at FIG. 5B. Considering the manner in which the collection of rays corresponding to projection S is reflected, it will be noted that in the reflected data set 511 the collection of values comprising line 507 have now been transformed into a diagonally-extending line 513, the end points of which are again the measured values A and B.

Of interest to note is that the full projection fan from an assumed reflection point X will not be generated until the source S has moved to the position S', which also implies (as aforementioned) that detector measurements will actually have to be made over twice the fan angle before the full reflected fan from X is generated.

Referring to data set 511, the same point becomes evident. It is thus seen that the projection from X which is indicated by line 515 cannot be effected until sufficient diagonals 513 are generated to enable production of that line 515. The vertical distance between B and A in data set 511, thus as mentioned, corresponds to twice the fan angle from source S.

In FIG. 4, in addition to rays A and B, several further rays C and D are depicted, i.e., these are additional rays within the fan beam. If one considers a ray such as C which intersects the detector array at a point X', the point X' can be regarded in accordance with aspects of this invention as a source for determining reflected data points. As previously discussed, however, the angle between rays A and C is predetermined by the actual geometry utilized and the geometrical reflection from X' may not in fact occur at a point at which reflected data is desired. To put this another way, in order to provide reflected data at a point of interest, it is frequently necessary pursuant to the invention, to use measurement data from a point appropriate for reflection to the point of interest. This can be effected by interpolating between measured data from the same detector at successive measuring projection angles.

This is illustrated in FIG. 5A, where measured data values 517 and 519 are shown for a representative detector, say detector element No. 5, for successive measuring projection angles. In order to attain reflection at a specifically desired point, the geometry of the CT system may dictate that reflection is not appropriate from either the angle corresponding to data value 517 or 519, but rather from a desired point Z intermediate the two points corresponding to 517 and 519. Accordingly, one effects an interpolation between the measured values at 517 and 519 in order to determine the value at the intermediate point Z, and it is this last value which is reflected pursuant to the invention.

It should further be understood, that where the invention is being applied to increase image resolution as aforementioned, the same interpolation technique is applicable. Typically in these instances one desires to produce reflection data from points intermediate the detector element positions during actual measuring projections. Hence, in effecting the reflection of measured data one interpolates, again between the data measurements taken by a given detector for successive measuring projections, whereby the reflection is to the points of interest. Effectively, the reflected data thus corresponds to detector element positions laterally displaced with respect to the positions thereof during the projections yielding the measured detector data. As aforementioned, the detector elements will in some instances be offset a quarter element from the center line between the detector means and source during the projections yielding the measurements; and in this instance the displacements should correspond to one-half of a detector element.

While the present invention has been particularly described in terms of specific embodiments thereof, it will be understood in view of the instant disclosure, that numerous variations upon the invention are now enabled to those skilled in the art, which variations yet reside within the scope of the present teaching.

Thus, while the present invention has been particularly described with reference to its application in a particular type of rotary CT system, it will be understood by those skilled in the art that the invention is applicable to any CT system wherein a penetrating radiation course and radiation detector means are used to effect measurements of plural sets of transmission values for multiple diverging transmission paths for said radiation in a quasi-plane containing an object slice being examined.

Accordingly, the invention is to be broadly construed, and limited only by the scope and spirit of the claims now appended hereto.

I claim:

1. In the method for constructing a two-dimensional representation of an object lying in a quasi-plane by positioning a radiation source for providing radiation in the form of a fan beam so that at least some of said radiation passes through said object; positioning detector means including an array of side by side detector elements opposite said source and aligned therewith and lying in said quasi-plane for detecting radiation in said quasi-plane not absorbed or scattered by said object; effecting relative rotation between said object and said source-detector combination about an axis of rotation such that said source and detector means remain in said quasi plane;

effecting measuring from said source at a plurality of angular positions during said rotation to obtain a multiplicity of measured data readings from said detector elements at each said projection;

and reconstructing a two-dimensional representation of the object by convolving said data without reordering of same, and scaling and back projecting same; THE IMPROVEMENT COMPRISING:

generating estimated detector data at desired projection angles by reflecting said measured detector data obtained during said projections; and performing said reconstruction step utilizing both said measured and said estimated detector data.

2. A method in accordance with claim 1, wherein said reflecting step includes adjusting the measured readings from each detector element by interpolating between successive readings from said detector element to yield the reading appropriate for geometrical reflection to said desired projection angle.

3. A method in accordance with claim 2, wherein said reflected data correspond to detector element positions laterally displaced with respect to the positions thereof during said projections yielding said measured detector data.

4. A method in accordance with claim 3, wherein said measured detector data from each measuring projection angle is stored and interleaved with the estimated detector data obtained by reflection and corresponding to the same projection angle, prior to said reconstruction step.

5. A method in accordance with claim 3, wherein said measured detector data from each measuring projection angle is interleaved with zeros and provided for said reconstruction step, and wherein estimated detector data obtained by reflection and corresponding to each measuring projection angle is interleaved with zeros and provided for said reconstruction step; whereby said reconstruction step is conducted as if operating upon data from an increased number of detector elements.

6. A method in accordance with claim 3, wherein said detector elements are offset $\frac{1}{4}$ element from the center line between said detector means and source during said projections yielding said measurements; and wherein the said displacements correspond to $\frac{1}{2}$ of a detector element.

7. In the method for constructing a two-dimensional representation of an object slice lying in a quasi-plane by utilizing a source of penetrating radiation and radiation-detector means to effect measurements of plural sets of transmission data for multiple diverging transmission paths in a quasi-plane containing an object slice being examined;

and reconstructing a two-dimensional representation of the object slice by convolving said data without reordering of same, and scaling and back projecting same; THE IMPROVEMENT COMPRISING:

generating estimated transmission data for desired transmission paths through said object by reflecting said measured transmission data; and performing said reconstruction utilizing both said measured ad said estimated transmission data.

8. In a system for constructing a two-dimensional representation of an object slice lying in a quasi-plane; said system including a radiation source positioned for providing radiation in the form of a fan beam so that at least some of said radiation passes through said object; detector means including an array of side by side detector elements positioned opposite said source and aligned therewith and lying in said quasi-plane for detecting radiation in said quasi-plane not absorbed or scattered by said object; means for effecting relative rotation between said object and said source-detector combination about an axis of rotation such that said source and detector means remain in said quasi-plane;

means for effecting measurements from said source at a plurality of angular positions during said rotation to obtain a multiplicity of measured data readings from said detector elements at each said projection;

and means for reconstructing a two-dimensional representation of the object by convolving said data without reordering of same, and scaling and back projecting same; THE IMPROVEMENT COMPRISING:

means for reflecting said measured detector data obtained during said projections to generate estimated detector data at desired projection angles; and means for providing both said measured and estimated data to said reconstructing means whereby said reconstruction is effected utilizing both said measured and said estimated detector data.

9. A system in accordance with claim 8, wherein said reflecting means includes means for adjusting the measured readings from each detector element by interpolating between successive readings from said detector element to yield the reading appropriate fro geometrical reflection to said desired projection angle.

* * * * *